United States Patent [19]

Seigneurin

[11] Patent Number: 4,661,062
[45] Date of Patent: Apr. 28, 1987

[54] DENTAL HANDPIECE CONTRA-ANGLE HEAD

[75] Inventor: Michel Seigneurin, Douvaine, France
[73] Assignee: Micro Mega S.A., Besancon, Switzerland
[21] Appl. No.: 776,431
[22] Filed: Sep. 16, 1985
[30] Foreign Application Priority Data
Sep. 14, 1984 [FR] France .................. 84 14730
[51] Int. Cl.⁴ .................................................. A61C 1/14
[52] U.S. Cl. ................................................... 433/128
[58] Field of Search .................. 433/126, 128, 127; 279/1 B, 74

[56] References Cited

U.S. PATENT DOCUMENTS 2,873,527  2/1959  Flatland ............................. 433/128
4,012,841  3/1977  Mosimann ......................... 433/127

Primary Examiner—Robert Peshock
Attorney, Agent, or Firm—Robert E. Burns; Emmanuel J. Lobato; Bruce L. Adams

[57] ABSTRACT

This contra-angle head of a dental handpiece comprises means for axially locking the dental instrument, in the form of a hollow guide member enclosing the upper portion of the driving pinion inside the head casing, this guide member being mounted for axial movement in the casing and rotating with the pinion by means of at least two wedge members disposed in the guide member and adapted to engage an annular groove of the dental instrument and to bear against the upper edge of this groove. A spring constantly urges the guide member away from the casing so that the instrument is pushed inwardly in the pinion by the wedge members for engagement with a shoulder formed in the pinion bore and acting as a stop means, the wedge members thus exerting a constant play take-up function.

8 Claims, 9 Drawing Figures

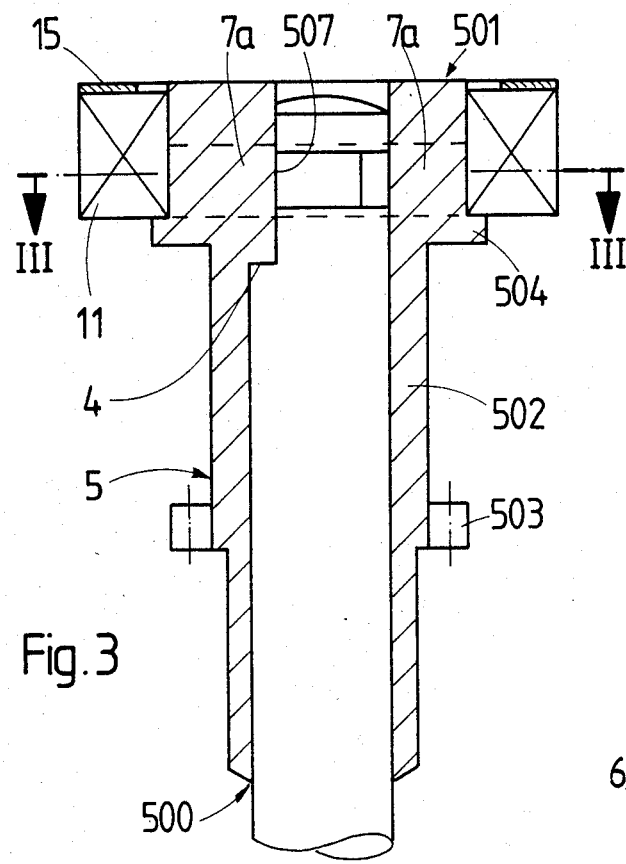
Fig.3
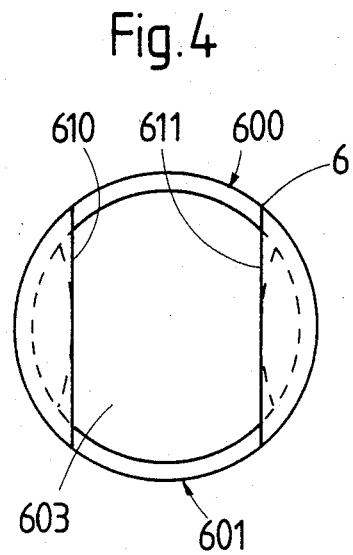
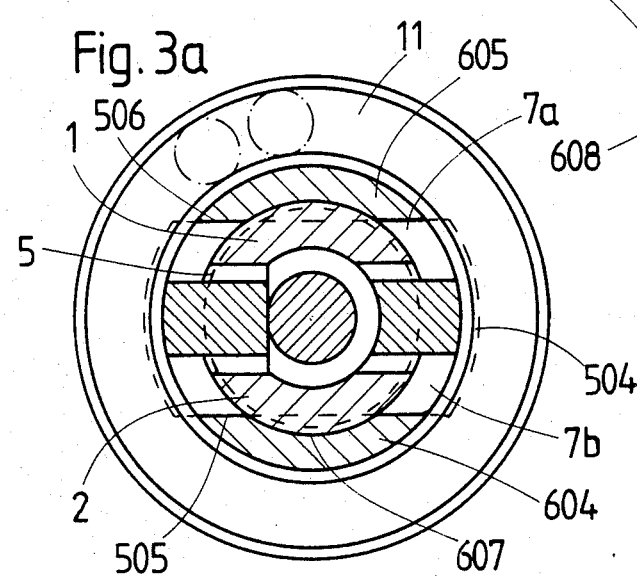
Fig.3a

DENTAL HANDPIECE CONTRA-ANGLE HEAD

BACKGROUND OF THE INVENTION

The present invention relates in general to contra-angle heads for dental handpieces and is directed more particularly to improved play taking means for devices of this character.

THE PRIOR ART

As a rule, the contra-angle head of a dental handpiece comprises a small, pivotally or slidably mounted bar engaging the groove normally provided in the bur shank, in order to lock the head against longitudinal movement without interfering with its rotation produced by the flat face projecting into the corresponding cavity of the head pinion.

The admitted tolerances for both the width of the bur shank groove and the thickness of the small bar to be engaged in this groove are such that in some specific cases the longitudinal play of the bur is rather detrimental because it becomes the source of longitudinal vibration when the bur operates against a hard material such as the enamel of a tooth.

BRIEF DESCRIPTION OF THE INVENTION

It is actually the primary object of the present invention to avoid the above-defined inconvenience to taking up this longitudinal play continuously while preserving the nearly instantaneous fixing of a dental instrument, notably a bur.

This object consists essentially in causing a longitudinal pressure to be exerted continuously by wedge members, preferably of semi-circular configuration, on the instrument shank, in order to eliminate any detrimental clearance. Moreover, with this arrangement, all the locking components of the device are housed in the upper portion of the contra-angle head, above the driving pinion, thus clearing this pinion as well as the surrounding space and eliminating any interference with the pinion drive.

Other features and advantages of the present invention will appear as the following description proceeds with reference to the accompanying drawings.

THE DRAWINGS

FIG. 3 is a longitudinal axial section showing the driving pinion;

FIG. 3a is a section taken along the line III—III of FIG. 3;

FIG. 4 is a plane view from beneath showing the guide socket, as seen in the direction of the arrow IV of FIG. 5;

FIG. 5 is a longitudinal axial section of the guide socket;

DESCRIPTION OF THE PREFERRED EMBODIMENT

Figure 1:
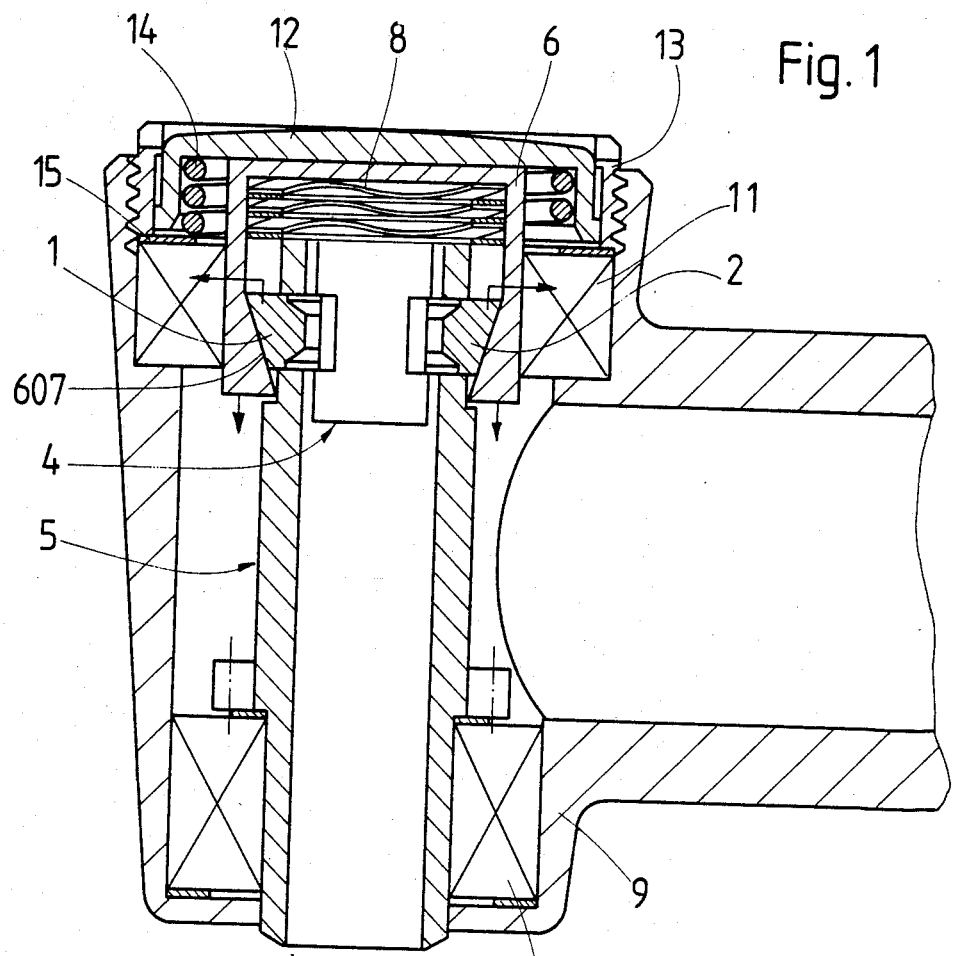
FIG. 1 illustrates in longitudinal axial section a preferred form of embodiment of the play taking device of the present invention, shown in its related condition.

Referring first to FIG. 1, showing in longitudinal axial section the contra-angle head 9 of a dental handpiece before inserting a bur or other dental instrument 30 corresponding to international standards, it will be seen that this instrument 30 comprises a shank 31 adapted to be fixed in the head 9 and provided with an annular groove 32 and a flat face 33 of a height slightly in excess to the width of said groove 32.

Figures 7, 8:
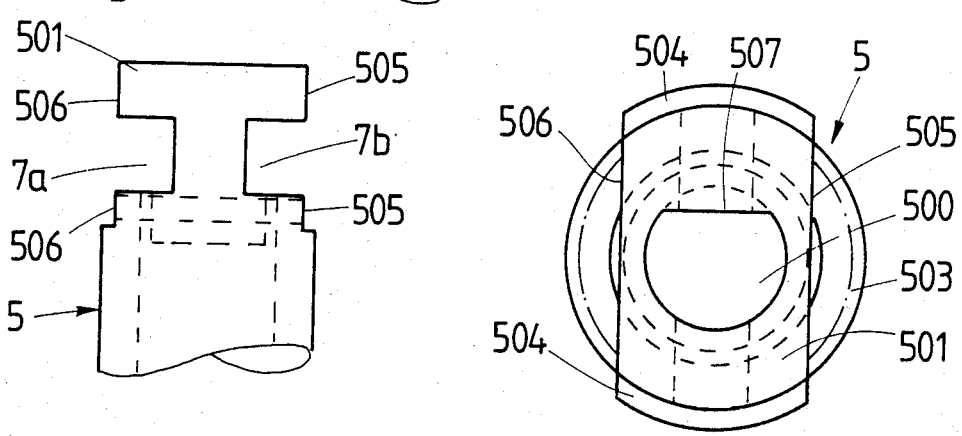
FIG. 7 is a plane view from above of the hollow pinion.
FIG. 8 is a side elevational view of the upper end of the pinion.

A hollow pinion 5 (FIGS. 3, 7 and 8) having a toothed annulus 503 fitted thereon comprises a bore 500 adapted to receive the dental instrument 30 up to a shoulder constituting in this bore an abutment 4 causing the flat face 33 of instrument 30 to coincide with an inner fluted flat face 507 of the upper portion 501 of said hollow pinion 5. As shown in FIG. 3, the bore 500 of pinion 5 comprises two longitudinal sections separated by said shoulder constituting the aforesaid depth limiting engageable by the flat face of the instrument. The upper bore section 501 receiving this shank 31 consists of a cylindrical portion concentric to the pinion shank 502, this cylindrical portion extending from the toothed annulus 503 to the upper section 501. The outer diameter of this cylindrical portion is greater than the outer diameter of the shank. Furthermore, this upper section 501 is machined to remove two equivalent cylindrical segments in order to provide two parallel flat faces 505, 506 (FIGS. 7 and 8). Formed through each flat face 505, 506 is a groove 7a, 7b extending at right angles to the longitudinal center line of pinion 5 and parallel to said flat faces 7a and 7b. The shoulder formed between the shank 502 and the upper section 501 constitutes a base surface 504 for a bearing 11.

The pinion 5 is rotatably mounted in the cavity of the contra-angle head 9 by means of a pair of plain bearings or ball-bearings 10 and 11. The pinion 5 is driven by means of a toothed wheel secured to the driving end of the handpiece driving shaft (not shown) and kept in meshing engagement with the pinion 503.

A hollow cylindrical guide socket 6 (FIGS. 4 and 5) is fitted over the upper portion 501 of pinion 5 and rotates therewith in the top bearing 11. This guide socket 6 is closed at one end by a cup or cover 603, the opposite end 609 being open.

Figure 6:
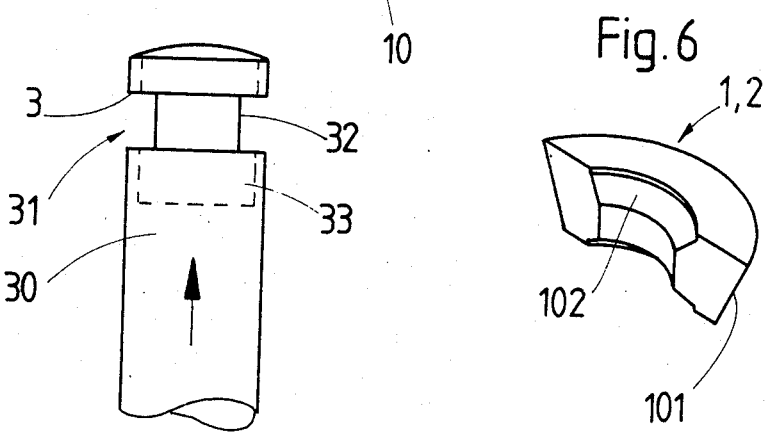
FIG. 6 is a perspective view of a wedge member.

This guide socket 6 has fitted in its bore 602 a pair of diametrally opposed semi-circular wedge members 1 and 2 (FIG. 6), so that wedge member 1 engages grooves 7a and wedge member 2 engages groove 7b of pinion 5 (FIG. 3a). Each wedge member 1,2 comprises an outer peripheral tapered surface 101 (FIG. 6) bearing on the side opposite the instrument shank 30 against a matching inner tapered surface 607 of said guide socket 6 (FIG. 6) constituting a ramp having its slope directed towards the bottom 603 of guide socket 6. The portion of each wedge member 1,2 which is directed towards the bur shank 30 is bevelled and formed with an inner tapered surface 102 (FIG. 6) bearing against the upper ledge 3 of groove 32 which is opposite the operating portion of instrument 30.

A pair of symmetrical, diametrally opposed notches 600,601 formed in the wall of the hollow cylindrical guide socket 6 (FIG. 4) separate this wall portion into two identical areas 604, 605 (FIG. 5) comprising in the bore 602 from the bottom 603 a cylindrical portion 606 and from an annular shoulder 608 a frustoconical portion 606a constituting the aforesaid tapered inner surface 607.

This frustoconical portion 606a is intersected by two flat faces 610 and 611 parallel to the longitudinal axis of guide socket 6 and coincident with the two notches 600,601 so as to define the width of opening 609, this width being equal to the distance between said flat faces 505 and 506 in the upper section 501 of pinion 5, so that when the wedge members 1 and 2 are inserted into grooves 7a and 7b and bear against the tapered surface 607 they cannot escape from the guide socket 6, since the flat faces 610 and 611 engage exactly the flat faces 505 and 506 of the upper section 501 of pinion 5.

Figure 2:
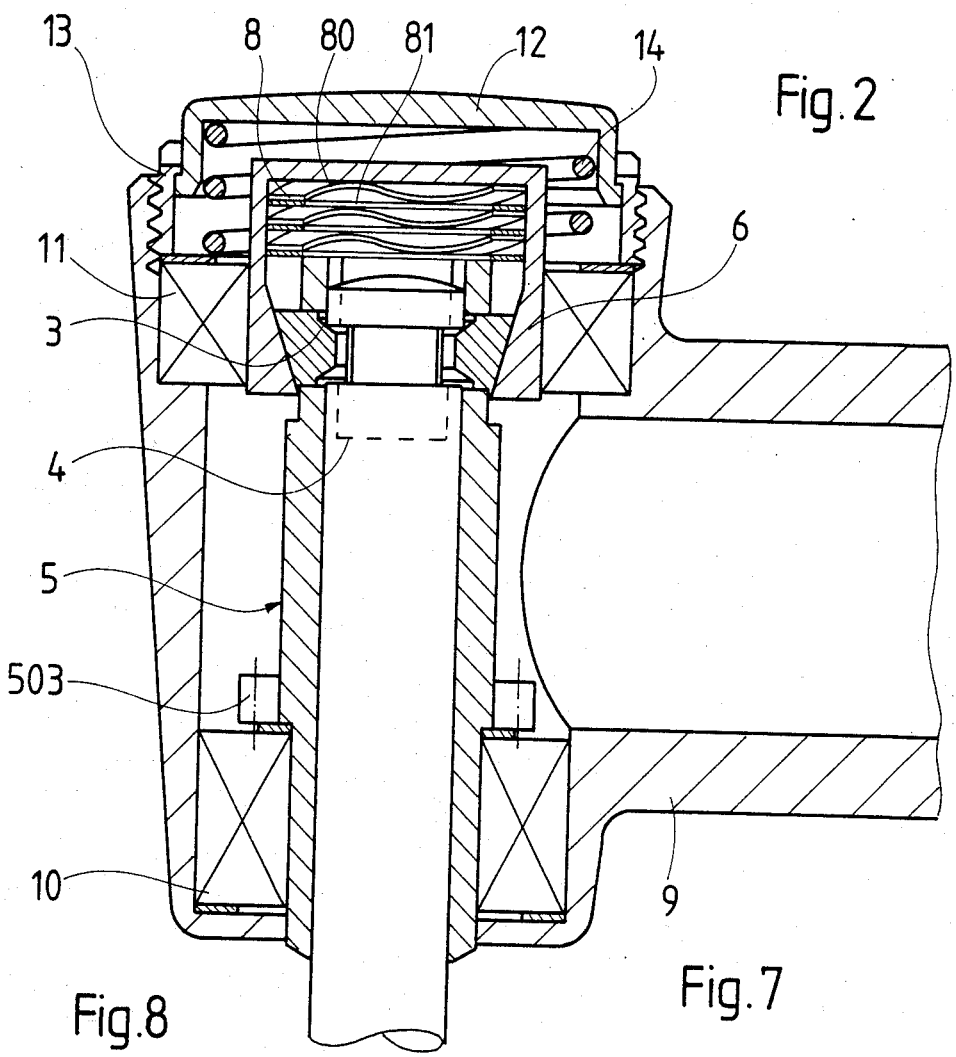
FIG. 2 is a view similar to FIG. 1 showing the device in its locked condition.

An annular composite spring 8 housed in guide socket 6 bears with one face against the bottom 603 of guide socket 6 and with the opposite face against the top face 501 of pinion 5 so as to exert a permanent resilient pressure thereagainst, therefore also during the rotation of pinion 5. This composite spring 8 consists preferably of alternate layers of flat or plain washers 81 and corrugated washers 80 with three contact points disposed at spaced intervals along their circumference. The pressure of spring 8 is also exerted against the ledge 3 of the groove 32 of instrument 30 since said wedge members 1,2 are pulled upwards by the inner tapered surface 607 of guide socket 6 while the instrument is retained by stop 4 in the bore of pinion 5. Thus, the instrument is free of any axial play (FIG. 2).

The longitudinal movement of guide socket 6 permitting the movement of wedge members 1 and 2 away from each other for introducing the instrument shank into the handpiece head 9 is controlled by a push-button 12 capping said guide socket 6 and held in position on the head 9 by an externally threaded ring nut 13 engaging corresponding internal threads formed in the head 9, as shown. A coil compression spring 14 reacts with one end against the inner bottom surface of push-button 12 and with the other end against a washer 15 supporting the bearing 11.

The instrument 30 is removed from the head 9 by simply depressing the push-button 12. In FIG. 1, this button 12 is shown in its depressed condition, in which it bears against guide socket 6. In this position, the inner tapered surface 607 of the socket releases both wedge members 1 and 2 so that they can yield laterally and the urged radially outwards by the ledge 3 of groove 32, thus freeing the passage for the shank of instrument 30 which can therefore be extracted from the pinion bore 500.

The lateral inward movement of wedge members 1 and 2 which is necessary for fixing the bur to pinion 5 is only a few tenth of mm. Similarly, the axial movement of guide socket 6 which is necessary for moving the wedge members is also extremely small.

When another instrument has been introduced into the bore 500 of shank 5, the push-button 12 is released. In FIG. 2, the pressure exerted on button 12 has been released and the button is moved upwards to its operative position in the head 9 by the resilient force of spring 14. Under these conditions, the guide socket 6 can move in the same direction but under the pressure of spring 8, whereby both wedge members 1,2, driven by the inner tapered surface 607, penetrate into the groove 32 of the instrument shank while exerting a pressure against the ledge 3 of this groove 32, so as to cause the ledge 3 to press with force the flat face 33 against the stop 4 in bore 500 of pinion 5.

When the instrument is rotatably driven by pinion 5, the spring 8 exerts a constant pressure and thus prevents the instrument from developping an excessive axial play, since the guide socket 6, spring 8 and wedge member 1,2 rotate with the pinion 5 in bearing 11. In the operative position (FIG. 2) the push-button 12 is pulled outwards by spring 14 and consequently does not contact the guide socket 6.

Of course, other forms of embodiment may be contemplated by those skilled in the art without departing from the basic principles of the invention as set forth in the appended claims.

What is claimed is:

1. Dental handpiece contra-angle head comprising a hollow pinion rotatably mounted in the head casing and adapted to have a dental instrument, notably a bur, fitted therein, said instrument having a shank provided with a flat face adapted to cooperate with a complementary flat face formed in the upper portion of said pinion so as to be rotatably coupled to said pinion, said shank further comprising an annular groove engageable, in the operative position of said instrument, by means for axially locking the instrument in said operative position, said locking means comprising a clamping member mounted in said head casing, movable along the axis of said casing and rotatably coupled to said pinion, at least two wedge members surrounded by said clamping member and provided with outer tapered surfaces adapted to engage a matching inner tapered surface said clamping member and also with inner tapered surfaces engaging an upper ledge of said annular groove of said instrument, respectively, and spring means constantly urging said clamping member axially outwards in said head so as to cause said instrument to be urged by said wedge members inwards in said pinion, characterized in that said pinion is provided with inner abutment means engageable by said instrument as a consequence of the resilient pressure exerted thereon by said wedge members, and that said clamping member consists of a hollow guide member enclosing the top portion of said pinion and having a bore bounded at the top by a bottom wall, and intermediate cylindrical side wall terminating at its lower end with frustoconical portion constituting said inner tapered surface, said spring means being housed in said cylindrical side wall and bearing with one end against said bottom wall and with the opposite end against the top portion of said pinion.

2. A contra-angle head according to claim 1, wherein a pair of symmetrical, diametrally opposed notches are formed in said intermediate cylindrical side wall of said guide member for separating said wall into two identical areas, said frustoconical portion being intersected by two flat faces parallel to the longitudinal axis of said guide member and determining the width of the aperture formed in said guide member opposite said bottom.

3. A contra-angle head according to claim 1, wherein said spring means comprise a plurality of washers provided with corrugations at three circumferentially spaced points and alternating with plain washers.

4. A contra-angle head according to claim 1, wherein said pinion comprises a bore divided into two sections by a shoulder constituting said abutment means determining the depth of said flat face of the instrument shank, the upper section engaged by said shank being cylindrical and concentric to the arbor of said pinion which separates said cylindrical section from a toothed portion, the diameter of said cylindrical section being greater than that of said arbor, said upper section being machined to remove two equivalent cylindrical segments therefrom and form two parallel flat faces of which the relative spacing corresponds to the width of the aperture of said guide member, the arbor section adjacent said upper section constituting a base for a bearing, each one of said parallel flat faces having formed therethrough a groove extending at right angles to the longitudinal center line of said pinion and parallel to said flat faces, said grooves being adapted to receive one portion of said wedge members.

5. A contra-angle head according to claim 1, wherein the end of the head casing which is opposite the end through which the instrument is fitted into the head comprises a push-button covering said guide member and adapted to slide in a ring nut engaging screw threads formed in said head casing, said ring limiting the stroke of said push-button which is caused by a return spring separating said ring nut from said guide member, said push button being actuatable for controlling the longitudinal movement of said guide member when it is desired to momentarily relieve the permanent pressure exerted by said spring on said guide member.

6. Dental handpiece contra-angle head comprising a head casing, a hollow pinion rotatably mounted in said head casing and adapted to receive a dental instrument, notably a bur, said instrument having a shank provided with a flat face complementary to a flat face formed in an upper portion of said pinion so as to be rotatably coupled to said pinion, said shank further comprising an annular groove near an end of said shank and an abutment limiting axial movement of said shank upwardly realtive to said pinion, and means for releasably locking said instrument in said pinion, said locking means comprising a a clamping member rotatably mounted in said head casing and embracing an end of said pinion, said clamping member having a tapered inner surface converging downwardly, at least two wedge members surrounded by said clamping member and having tapered outer surfaces engaging said tapered inner surface of said clamping member and tapered inner surfaces engageable with an upper edge of said annular groove of said shank of said instrument and spring means acting between said clamping member and an upper end of said pinion to urge said clamping member upwardly relative to said pinion to urge said wedge members inwardly by engagement of said tapered inner surface of said clamping member with said tapered outer surfaces of said wedge members and to urge said pinion and said shank of said instrument downwardly relative to said clamping member and wedge members, whereby said instrument is held against axial movement relative to said pinion by engagement of said tapered inner surfaces of said wedge members with said annular groove in said shank of said instrument preventing downward axial movement of said shank relative to said pinion and said abutment of said shank preventing upward movement of said shank relative to said pinion.

7. A contra-angle head according to claim 6, in which said spring means comprises alternate layers of flat washers and corrugated washers.

8. A contra-angle head, according to claim 6, further comprising a cup-shaped push-button capping said clamping member and manually operable to move said clamping member downwardly relative to said pinion to permit radially outward movement of said wedge members to release said instrument.

* * * * *